(12) United States Patent
Duckett, III

(10) Patent No.: US 11,294,166 B2
(45) Date of Patent: *Apr. 5, 2022

(54) ENDOSCOPE INCORPORATING MULTIPLE IMAGE SENSORS FOR INCREASED RESOLUTION

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

(*) Notice: Subject to any disclaimer, the term of this patent is extended or adjusted under 35 U.S.C. 154(b) by 47 days.

This patent is subject to a terminal disclaimer.

(21) Appl. No.: 16/733,999

(22) Filed: Jan. 3, 2020

(65) Prior Publication Data

US 2020/0142179 A1 May 7, 2020

Related U.S. Application Data

(63) Continuation of application No. 15/400,137, filed on Jan. 6, 2017, now Pat. No. 10,571,679.

(51) Int. Cl.
*H04N 5/225* (2006.01)
*G02B 23/24* (2006.01)
(Continued)

(52) U.S. Cl.
CPC ...... *G02B 23/2484* (2013.01); *A61B 1/00009* (2013.01); *A61B 1/00096* (2013.01);
(Continued)

(58) Field of Classification Search
None
See application file for complete search history.

(56) References Cited

U.S. PATENT DOCUMENTS 4,940,309 A * 7/1990 Baum ................. G02B 27/145
359/618
5,194,959 A 3/1993 Kaneko
(Continued)

FOREIGN PATENT DOCUMENTS

| EP | 1429540 A1 | 6/2004 |
| JP | S6088924 | 5/1985 |
| WO | WO199418789 | 8/1994 |

OTHER PUBLICATIONS

European Search Report, Munich, Germany, dated Jul. 3, 2018; Application No. 18150273.3-1124.
(Continued)

*Primary Examiner* — Shadan E Haghani
(74) *Attorney, Agent, or Firm* — Michael J. Loi; David Noel Villalpando

(57) ABSTRACT

An endoscope or other endoscopic instrument is provided with multiple image sensors incorporated into the distal tip, each capturing a portion of the image provided from an optical imaging system. The output from the multiple sensors is combined and manipulated into a single high resolution image which can then be displayed to the user. A virtual horizon rotation feature is also provided which can rotate a displayed image within a combined field of view including data from the multiple image sensors. Various light directing element designs are provided to direct image light to the multiple sensors.

13 Claims, 10 Drawing Sheets

(51) Int. Cl.
*G02B 23/10* (2006.01)
*G02B 23/04* (2006.01)
*A61B 1/00* (2006.01)
*A61B 1/05* (2006.01)
*G06T 3/40* (2006.01)

(52) U.S. Cl.
CPC ...... *A61B 1/00179* (2013.01); *A61B 1/00188* (2013.01); *A61B 1/051* (2013.01); *G02B 23/04* (2013.01); *G02B 23/10* (2013.01); *G02B 23/243* (2013.01); *H04N 5/2256* (2013.01); *H04N 5/2258* (2013.01); *G06T 3/4038* (2013.01); *H04N 2005/2255* (2013.01)

(56) References Cited

U.S. PATENT DOCUMENTS

| | | | |
|---|---|---|---|
| 5,689,365 A | | 11/1997 | Takahashi |
| 6,366,315 B1 * | | 4/2002 | Drescher ............... H04N 1/03 |
| | | | 348/207.99 |
| 6,476,851 B1 | | 11/2002 | Nakamura |
| 6,659,940 B2 * | | 12/2003 | Adler ............... A61B 1/00096 |
| | | | 600/109 |
| 7,211,042 B2 | | 5/2007 | Chatenever |
| 7,372,642 B2 | | 5/2008 | Rohaly |
| 7,746,568 B2 | | 6/2010 | Rohaly |
| 8,360,964 B2 | | 1/2013 | Ertas |
| 8,928,746 B1 | | 1/2015 | Stevrin |
| 9,395,617 B2 * | | 7/2016 | McCain ............... G02B 13/06 |
| 9,557,634 B2 | | 1/2017 | Cheng |
| 10,165,183 B2 * | | 12/2018 | Georgiev ........... G02B 13/0065 |
| 2001/0022858 A1 | | 9/2001 | Komiya |
| 2004/0001145 A1 | | 1/2004 | Abbate |
| 2012/0053407 A1 | | 3/2012 | Levy |
| 2012/0057000 A1 | | 3/2012 | Rohaly |
| 2012/0320165 A1 | | 12/2012 | Schuck |
| 2013/0041226 A1 | | 2/2013 | McDowell |
| 2014/0098429 A1 | | 4/2014 | Morita |
| 2014/0313316 A1 * | | 10/2014 | Olsson ............ H04N 5/232945 |
| | | | 348/84 |
| 2014/0364694 A1 * | | 12/2014 | Avron ............... A61B 1/00181 |
| | | | 600/164 |
| 2014/0375784 A1 | | 12/2014 | Massetti |
| 2015/0062299 A1 | | 3/2015 | Brown |
| 2016/0037082 A1 | | 2/2016 | Wang |
| 2016/0057405 A1 | | 2/2016 | Duckett |
| 2017/0155818 A1 | | 6/2017 | Bonnet |

OTHER PUBLICATIONS

European Search Report, Munich, Germany, dated Nov. 6, 2018; Application No. 18150273.3-1124.

* cited by examiner

ENDOSCOPE INCORPORATING MULTIPLE IMAGE SENSORS FOR INCREASED RESOLUTION

CROSS-REFERENCE TO RELATED APPLICATIONS

This application is a continuation of U.S. patent application Ser. No. 15/400,137, filed Jan. 6, 2017, and entitled "Endoscope Incorporating Multiple Image Sensors for Increased Resolution," which is incorporated herein by reference.

BACKGROUND OF THE INVENTION

Field of the Invention

This invention relates to high resolution video endoscopes, and in particular to a scope using multiple sensors to create high resolution images.

Description of the Background Art

The invention relates to optical instruments such as endoscopes, exoscopes, and borescopes having an image sensor assembly at the distal end of the instrument shaft. More particularly, the invention relates to image sensing systems that can produce a combined image from multiple image sensors located within the distal end of the instrument shaft, and to optical instruments incorporating such image sensing systems.

Instruments such as endoscopes and borescopes are used to allow a visual inspection of locations which are not readily accessible. For example, endoscopes are typically (although not exclusively) used in medical applications to provide a view of an area within a patient's body. Whether employed for medical or other applications, the instrument typically includes an elongated shaft of relatively small diameter extending from a handle to a distal end.

An imaging or viewing arrangement is included with the instrument to allow a user to obtain a view from the shaft distal end. This arrangement may include a system of lenses and a light conduit through the shaft to direct an image from the distal end to an eyepiece associated with the instrument handle. Alternatively, the imaging or viewing arrangement may include an electronic imaging device at the distal end of the instrument shaft. Such an electronic imaging device collects image data and communicates that data through the shaft and handle ultimately to a processing system that assembles the data to produce an image displayed on a suitable display device.

Depending upon the procedure for which the instrument is used, it may be necessary for the operator to view a relatively large area, or view a relatively small area from different angles. In a medical procedure for example, the operator may desire to view a location which is larger than the field of view of the imaging collecting arrangement of the endoscope or view a location from different angles. In these situations, it has been necessary for the endoscope operator to move the distal end of the endoscope in an effort to provide the desired views, and sometimes move the distal end repeatedly in given area.

Endoscopes have been developed to give the operator the ability to adjust viewing angle. U.S. Patent Application Publication No. 2015/0238068 discloses an endoscope having an objective lens and prism that is mounted on a pivotable structure at the distal end of the endoscope. This endoscope, however, allows rotation to only one side of the device. Thus, the endoscope had to be repositioned in the area of the procedure in order to view a location on the opposite side of the endoscope shaft.

U.S. Publication No. 2014/0012080 shows another endoscope with an image collecting part which may be tilted to one side of the endoscope at the distal end. This arrangement also requires the endoscope distal end to be repositioned to obtain views of areas on the opposite side of the endoscope shaft (that is, opposite the side to which the image collecting device is tilted at a given point in time).

A flexible endoscope that allows panning the image without moving the scope tip is found in U.S. Pat. No. 8,771,177B2 to Hale et al., which is commonly owned with the present invention. This scope uses a wide angle lens positioned at an angle to the center axis of the scope to focus light from the front and sides of the scope. The light is focused on a high resolution sensor, along which a desired area is selected to produce an image that can be digitally panned along the range of view covered by the wide angle lens. The scope shaft is flexible and the high resolution sensor is positioned in a distal end portion of the shaft.

U.S. Pat. No. 8,360,964 to Ertas describes a wide angle HDTV endoscope includes at least two optical imaging channels. Two lenses are present at the scope distal tip, having different fields of view in complementary directions. Received images are transmitted along separate optical channels along the longitudinal axis of the endoscope to a single camera head that contains a wide screen image sensing device.

U.S. Publication No. 2015/0062299 describes a relatively large endoscope including two electronic-cameras arranged side-by-side facing along scope axis to create stereo picture pairs to permit quantitative 3-dimensional (3D) imaging and analysis.

U.S. Pat. Nos. 7,783,133 and 7,211,042, and U.S. Publication No. 2014/0375784 describe various techniques to counter-rotate an image produced from an endoscope image sensor and thereby achieve a constant, user-defined horizon.

Image sensors with desirably high resolution can be too large to fit into the distal tip of an endoscope. This problem often limits image resolution for endoscopes. With sensors available at the time of filing, an HD (1080p) sensor of adequate quality can be fit inside a scope shaft of a 10 mm diameter.

There remains a need for ways to provide higher resolution capabilities for endoscopes. There also remains a need in the art to provide an optical instrument such as an endoscope that allows the imaging device to be adjusted so that different views can be obtained without having to move the instrument distal end, or at least limiting the amount to which the distal end must be moved in a given procedure.

SUMMARY OF THE INVENTION

It is therefore an object of the invention to provide higher resolution and improved image manipulation for endoscopes having distal-tip image sensors. This invention is an endoscope that has multiple image sensors, each capturing a portion of the optical image provided by an optical imaging system. The output from the multiple sensors is combined and manipulated into a single high resolution image which can then be displayed to the user. A virtual horizon rotation feature is also provided which can rotate a displayed image within a combined field of view including data from the multiple image sensors. Various light directing element designs are provided to direct image light to the multiple sensors.

According to a first aspect of the invention, an endoscopic instrument for receiving an optical image includes an optical channel assembly positioned at the distal end portion of the endoscope shaft with a longitudinal axis spanning distal and proximal sides of the distal end portion. An objective lens with negative optical power is positioned in the distal end portion to receive image light from an object space and pass the image light toward the proximal side. The lens is typically a plano-convex singlet, but may have another optical configuration.

First and second image sensors are positioned in the instrument shaft distal end portion, the first image sensor positioned to receive a first portion, but not all, of the image light corresponding to a first area of an optical image, and the second sensor positioned to receive a second portion of the image light corresponding to a second area of the optical image. The second area is at least substantially different from the first area.

A first light directing element is positioned in an image space of the optical channel assembly to receive the first portion of the image light from the optical channel assembly and direct said portion toward the first image sensor. The first image sensor is positioned such that the light directed toward the first image sensor by the first light directing element is imaged onto the first image sensor.

In a first implementation according to the first aspect, a second light directing element is positioned in the image space to receive at least the second portion of the image light and direct it toward the second image sensor, wherein the second image sensor is positioned such that the light directed by the second light directing element is imaged onto the second image sensor In some implementations according to the first aspect or implementation, the first light directing element is implemented as a prism or a mirror. The first light directing element may also be a beam splitting prism in some versions.

In another implementation according to the first aspect or above implementations, the optical channel assembly further includes a single channel imaging system having one or more lenses optically arranged between the objective lens and the image sensors for passing the image light toward the image sensors by directing it to the image space where it is redirected to the image sensors.

In some implementations according to the first aspect or above implementations, the images on the first and second image sensors at least substantially overlap. For example, the first portion and second portion of the image light overlap such that each image sensor receives the same area of the image contained within the overlap.

In some implementations according to the first aspect or above implementations, the first and second image sensors at least substantially overlap. In other words, the second image sensor occupies a space that is mostly (or completely) directly above, in a direction that is non-parallel to the longitudinal axis, the first image sensor.

In some implementations according to the first aspect or above implementations, a processing unit is operatively coupled to the first and second image sensors to receive first and second image data from the sensors and operable to combine images from the first and second image data into a displayed image of higher resolution than that possible with the first sensor alone or the second sensor alone. The processing unit may be further operable to, when a user rotates the endoscopic instrument around its shaft, rotate a displayed image to provide a view with a constant horizon. In optical instrument system embodiments, the processing unit may reside, for example, within a camera head or camera control unit.

In some implementations according to the first aspect or above implementations, the first and/or second image sensors is/are positioned between 3 mm and 15 mm away from the objective lens.

In some implementations according to the first aspect or above implementations the first and/or second image sensors is/are arranged substantially parallel with respect to the longitudinal axis.

In some implementations according to the first aspect or above implementations, a third image sensor is arranged between the first and the second image sensors. The first, second, and third image sensors may at least substantially overlap in a direction that is non-parallel to the longitudinal axis.

In some implementations according to the first aspect or above implementations, the field of view of the optical channel assembly is at least 60 degrees. In wide-angle implementations, the optical channel assembly is a wide-angle lens system and may have a field of view between 60 and 180 degrees.

According to a second aspect of the invention, a method is provided for imaging through an endoscope. The method includes receiving image light at a distal lens of an optical assembly and passing the image light through a single optical channel path toward an image space within a distal end of the endoscope. The method further includes receiving a first portion of the image light with a first image sensor positioned in the endoscope distal end, forming a first image of a first part of the field of view of the distal lens, and receives a second portion of the image light with a second image sensor, the second portion of the image light forming a second image of a second part of the field of view of the distal lens, the second part of the field of view at least substantially different from the first part of the field of view.

The method further includes combining the first and second images to produce an image of higher resolution than would otherwise be possible with a single sensor. The method may perform image processing to align image data from the two images to allow combining them for a combined image stream.

In a first implementation according to the second aspect, the method further includes redirecting the first portion of the image light to the first sensor at a non-zero angle to a longitudinal axis spanning the distal end portion. The angle of redirection may be approximately 90 degrees.

In another implementation according to the second aspect or above implementation, redirecting the first portion of the image light is performed with a prism. Redirecting the first portion of the image light may also be performed with a beam splitting prism.

In another implementation according to the second aspect or above implementations, the first and second partial fields of view partially overlap.

In another implementation according to the second aspect or above implementations, the method further includes, in response to a user rotation of the endoscopic instrument around its shaft, conducting image processing to create an image with a constant horizon and of higher resolution than would otherwise be possible with a single sensor. The method may also include detecting the user rotation with at least one position sensor in the endoscope.

According to a third aspect of the invention, an optical instrument system includes an endoscopic instrument according to any of the above aspects and implementations and a camera control unit adapted to receive data from the endoscopic instrument and may be further adapted to perform one or more of the above implementations. For example, the camera control unit may include a processing unit to perform image processing for implementing a constant horizon rotating function. The optical instrument system may further include an electronic display for receiving a video signal.

Further scope of the applicability of the present invention will become apparent from the detailed description given hereinafter. However, it should be understood that the detailed description and specific examples, while indicating preferred embodiments of the invention, are given by way of illustration only, since various changes, combinations and modifications within the scope of the invention, as defined in the claims, will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE DRAWINGS

As used herein, elements (e.g., sensors and lenses) that are "optically arranged" in relation to other elements, refers to the elements' position along an optical path shared by first and other elements. For example, a relay lens group optically arranged between an image sensor and an objective, means that the relay lens group occupies a portion of the optical path that light travels (i.e., from the objective to the image sensor) for capturing images or video. "Optical image" is an image formed by the light rays from a self-luminous or an illuminated object that traverse an optical system or element.

Figure 1:
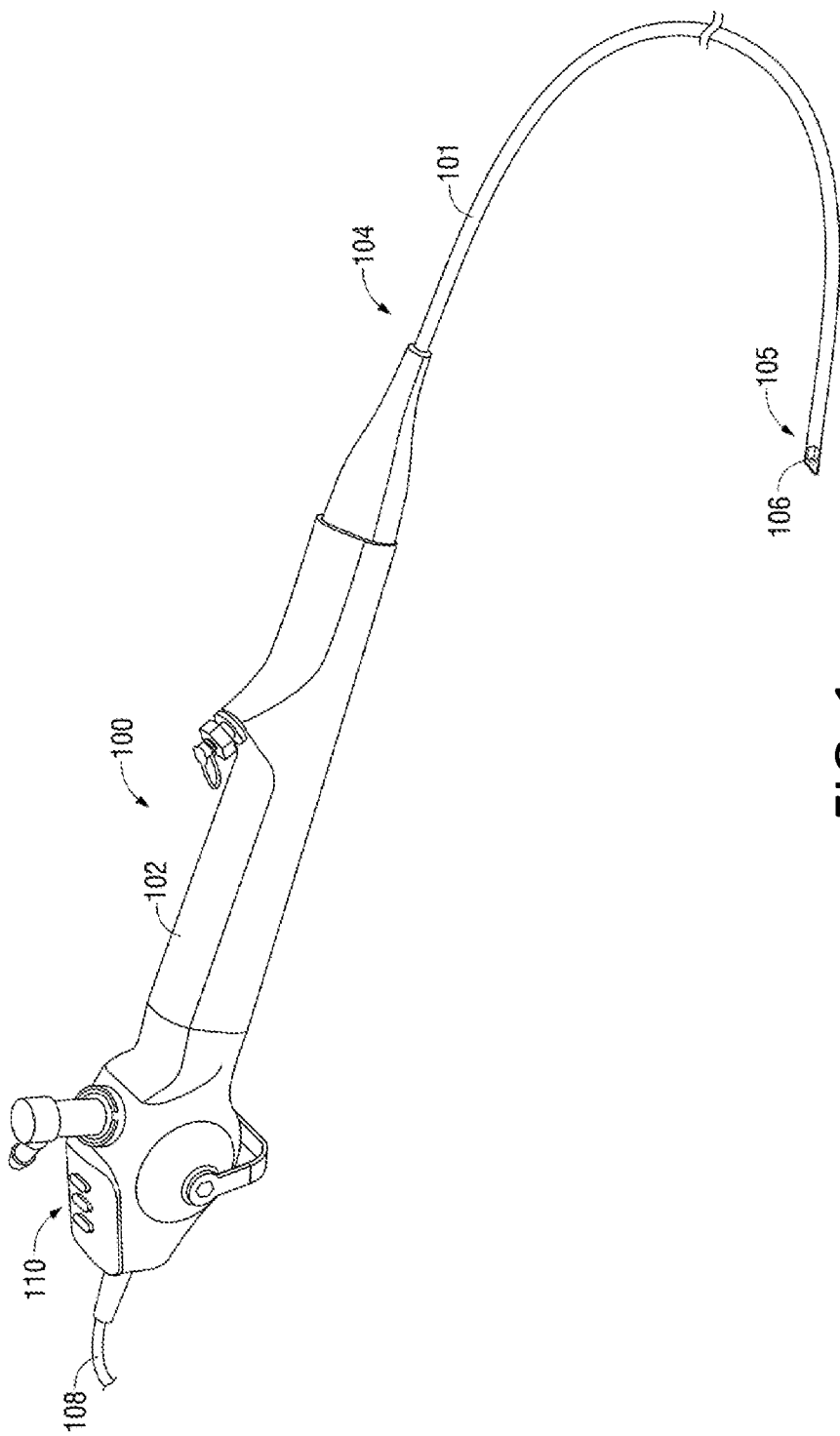
FIG. 1 is a perspective view of an endoscope instrument according to an example embodiment.

Referring to FIG. 1, depicted is a perspective view of an instrument 100 employing multiple distal image sensors according to one aspect of the present invention includes an elongated shaft 101 and a handle 102. Shaft 101 extends from a proximal end shown generally at reference numeral 104 connected to handle 102 to a distal end generally indicated at reference numeral 105. A distal end portion 106 is included at the shaft distal end 105. The image sensors according to the present invention are located in distal end portion 106, although it is not shown in FIG. 1 due to the scale of the figure. The shown shaft 101 is a flexible implementation, but rigid-shaft implementations are also possible.

Instrument 100 receives electrical operating power through a cable 108 which extends from a proximal end of handle 102 in this example instrument. This power may be used to operate one or more light sources and other electronic elements mounted within distal end portion 106, including multiple electronic image sensors. Also, data signals from such an imaging device may be communicated through appropriate conduits within shaft 101 and handle 102 to cable 108. These data signals may be communicated through cable 108 to processing equipment (not shown) which processes the image data and drives one or more video monitors to display the images collected at distal end 105 of instrument 100. Those familiar with endoscopes and borescopes will appreciate that instrument 100 includes a number of additional features such as controls 110 for controlling the operation of the instrument. Although data transmission relating to the image sensors will be described further below, the general operation and control of instrument 100 will not be described further herein in order to avoid obscuring the present invention in unnecessary detail. Preferably the designs and techniques herein are employed as improvements to a videoendoscope with a distal mounted image sensor arrangement, such as, for example, the videoendoscope described in U.S. Pat. No. 8,814,782 to Hale, et al, issued Aug. 26, 2014, which is hereby incorporated by reference.

Figure 2A:
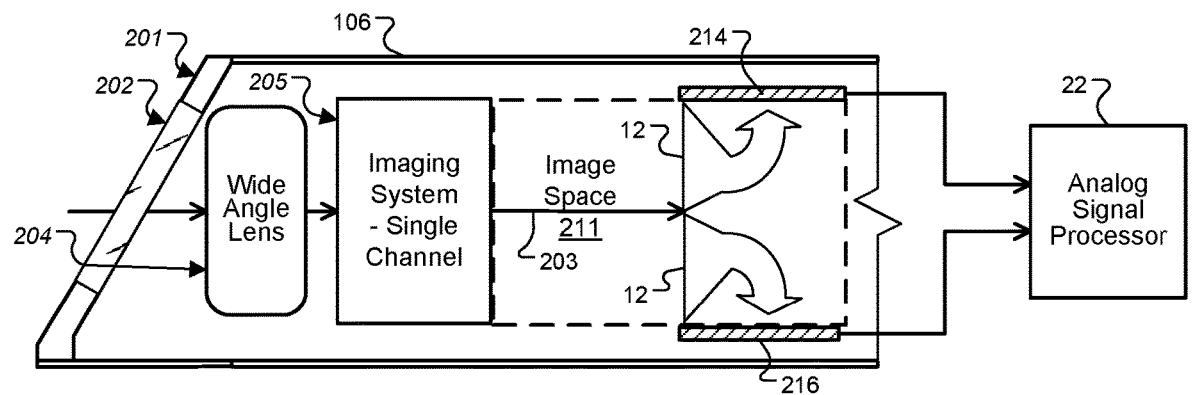
FIG. 2A is a cross section block diagram of a distal end of a shaft according to an example embodiment of the invention.

Referring to FIG. 2A, this figure shows a cross section block diagram of a distal end of a shaft according to an example embodiment of the invention. Depicted is the distal end portion 106 of shaft 101 having a cover glass 202 in an inset position at its distal face 201. Optically arranged at the interior side of cover glass 202 is an optical channel assembly positioned in the distal end portion 106, including an objective lens with negative optical power 204 having distal and proximal sides positioned to receive image light from an object space (the area to be imaged) at the distal side of lens 204 and pass the image light to the proximal side.

In wide-angle implementations, the field of view of the optical channel assembly may be between 60 and 180 degrees. Wide-angle implementations may include a fisheye lens as an optical element of a wide-angle lens system. The wide-angle lens system may be partially- or fully-defined by the optical channel assembly.

In the embodiment shown, cover glass 202 and lens 204 are fixed at a 30 degree angle from the scope axis, however in other versions no angle may be used or some other angle such as 45 degrees may be used. The optical channel assembly typically includes lens 204 and a single channel imaging system 205 of one or more prisms, lenses, lens groups, or other optical elements optically arranged at the proximal side of lens 204 to receive the image light as a beam and focus, disperse, or otherwise modify the beam. By "single channel", it is meant that a beam of light forming a single image is passed through a common lens group or set of optical elements with a single perspective.

Figure 2B:
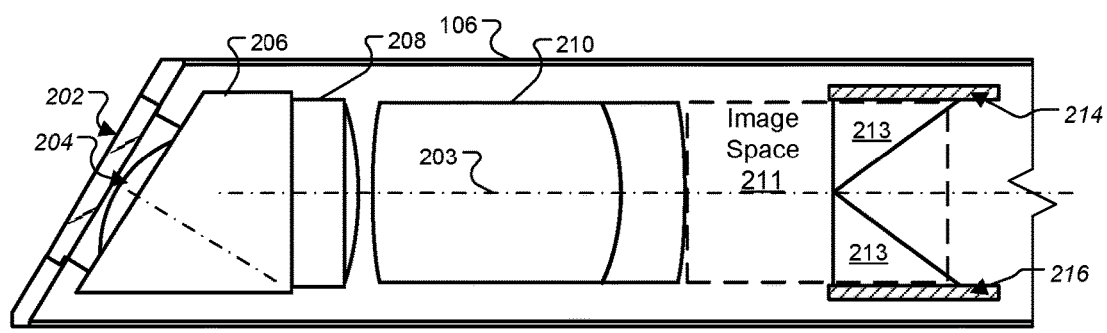
FIG. 2B shows a more detailed example design of a scope distal end portion according to another embodiment.

The optical channel assembly, an example version of which is further described with respect to FIG. 2B, generally directs the light toward an image space 211 at the distal end of the optical channel assembly 205. While the space is depicted as a gap in the drawings, a smaller gap or no gap may be present in some implementations. At least two image sensors 214 and 216 are positioned in the distal end portion 106 to receive light from the image space.

The upper depicted image sensor 214 is positioned to receive a first portion, but not all, of the image light corresponding to a first area of an image observed by the endoscope being redirected by light directing element 12 in the image space of the optical channel assembly, and the second sensor 216 is positioned to receive a second portion of the image light redirected in the image space 211 by the second depicted light directing element 12 and corresponding to second, different area of the image.

The light directing elements 12 may be any suitable element for redirecting light, such as a prisms, mirrors, light splitters or beam splitters, or fiber optic elements. Prisms are preferred because of their small size, mechanical durability and resistance to deformity.

As can be seen in this example version, the first image sensor 214 is positioned with a sensor array pointing to receive light propagating along a local optical axis non-parallel to the longitudinal axis of the endoscope shaft 203 of the optical channel assembly. In this figure, the sensor array is oriented substantially parallel to a longitudinal axis of the instrument shaft. In a conventional arrangement, shown in FIG. 3A, a sensor array is positioned perpendicular to the optical axis of the lens group providing the optical image for the array.

The arrangements shown in the other figures, in contrast, allow for sensors of a greater active array area (e.g., a light sensing area) than would ordinarily be possible to be fit into the endoscope shaft. Although in FIGS. 2A and 2B image sensors 214 and 216 are oriented parallel to the longitudinal axis of the endoscope 203, with their sensor arrays oriented for receiving light propagating along a local optical axis perpendicular to the longitudinal axis of the endoscope 203, other non-parallel image sensor pointing angles may be used. For example, one or both the sensor arrays may be pointed for receiving light redirected at 45 degrees from the longitudinal axis of the endoscope, at 30 degrees, or at 60 degrees.

Image sensors 214 and 216 typically are part of at least one sensing module or assembly that includes a printed circuit board ("PCB") on which is mounted an imaging device including an image sensor with sensing array, typically having a transparent cover. The PCB or other electrical circuitry that reads the sensed signal off the image sensing array of the sensors may be of any suitable type, preferably the smallest and lowest profile available to fit in the limited space. The various portions of the sensor assembly are known and are not shown separately. It will be appreciated by those familiar with imaging sensors that these devices may be accompanied by electronic components such as transistors, capacitors, resistors, and regulators for example.

Additionally, imaging sensors 214 and 216 and their accompanying electronic components require electrical power and means for communicating image data to be processed for producing the collected images. The required operating power and data transmission may be provided through a suitable electrical cable or bus connection. These accompanying electronic components and the power/data cable are omitted from the present drawings in order to more clearly illustrate the various features of the imaging apparatus.

Those skilled in the art will appreciate that the electronic components and power/data cable may be connected to or included with the image sensor modules in any number of fashions. For example, some embodiments may include the electronic components mounted on the opposite side of PCB on which imaging sensor itself is mounted. The power/data cable may also be connected to the back side of PCB to provide operating power to the image sensors and allow image data to be communicated from the image sensor assembly to processing equipment remote from the shaft distal end portion 106. However, the present invention is not limited to any particular mounting arrangement for electronic components which may accompany imaging sensor and a power/data connection. Any accompanying electronic components and the power/data cable need only be mounted to provide the required function.

Further, although sensors 214 and 216 are shown as discreet entities, two or more of the sensors may be share, for example, a mounting substrate or housing accommodating the two or more sensors.

In FIG. 2A, the image sensors 214 and 216 are connected through a power and data connection to an analog signal processor 22, which receives the analog sensor data and conditions it for processing by the digital portions of the system, as will be further described below. An analog signal processor 22 may be located in the handle 102 (FIG. 1) of the scope device, but may be located elsewhere. It is understood that metal oxide semiconductor sensors (CMOS) type sensors may have incorporated with the sensor assembly some of the digitization functions, however an analog signal processor 22 may provide further signal processing and control is needed before the image data is suitable for digital processing.

FIG. 2B shows a more detailed example design of a scope distal end portion 106 according to another embodiment. Behind the cover glass 202 is shown a preferred position for lens 204, set against or very near cover glass 202 and preferably assembled together with the cover glass in construction and then inserted into a gap in the scope tip from the proximal side and set in place. The single-channel imaging system in this embodiment includes a deflecting prism 206, or other suitable compound prism or combination of prisms, optically arranged or attached at the proximal side of lens 204 to receive the incoming light rays and deflect them along the longitudinal axis of the endoscope shaft.

Figure 2C:
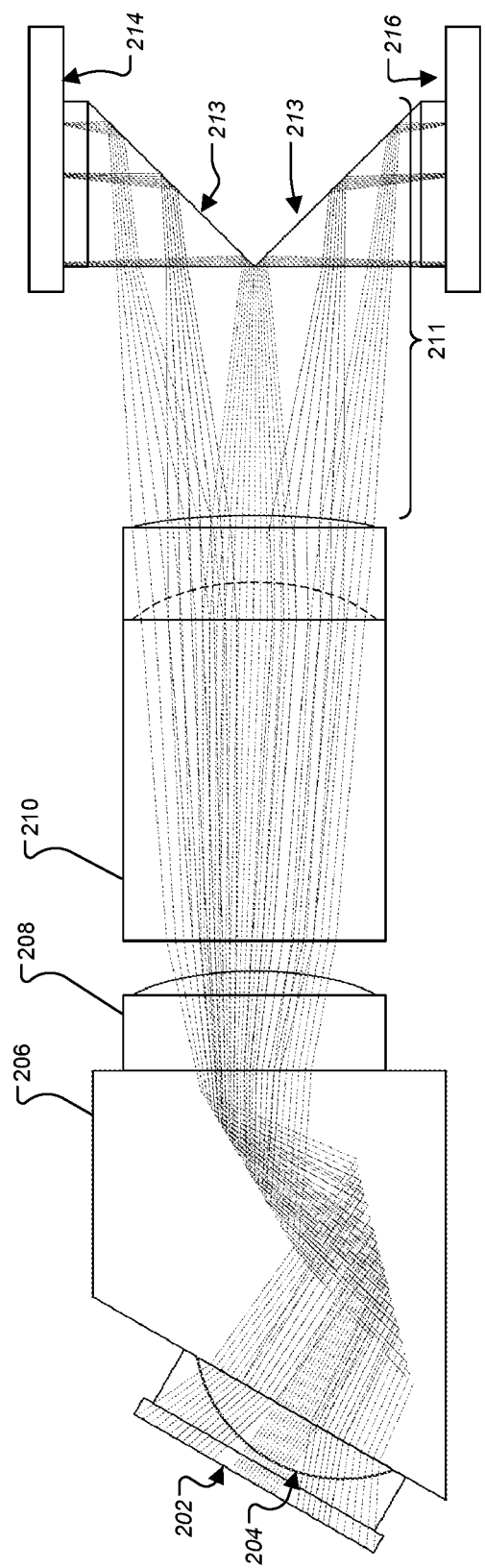
FIG. 2C shows a light ray bundle diagram for a system like that of FIG. 2B.

This effect can be seen in the diagram of FIG. 2C which shows a light ray bundle diagram for a system like that of FIG. 2B (not to scale). Optically arranged or attached at the proximal side of deflecting prism 206 is a lens 208, preferably a convex singlet lens as depicted, to spread the incoming light to an appropriate size for the imaging process downstream in the proximal direction. Next the light is received at an achromatic doublet lens 210, or other suitable lens, and directed outward to the image space 211. While this particular optical channel assembly is preferred, any other suitable optical assembly may be used to prepare the incoming light for reception by the image sensors.

At the image space 211, the light emerges from the single channel optical system described in parallel or near-parallel rays. In this embodiment, the image light is directed to the sensors 214 and 216 by right angle prisms 213, which are one example of light directing elements 12.

This arrangement receives a first portion of the image light from the optical channel assembly with the first image sensor 214, the first portion of the image light forming a first image of a first part of the field of view of the (single) optical channel assembly, and receives a second portion of the image light from the optical channel assembly with the second image sensor 216, the second portion of the image light forming a second image of a second part of the field of view of the optical channel assembly, the second part of the field of view substantially different from the first part of the field of view.

Figure 4A:
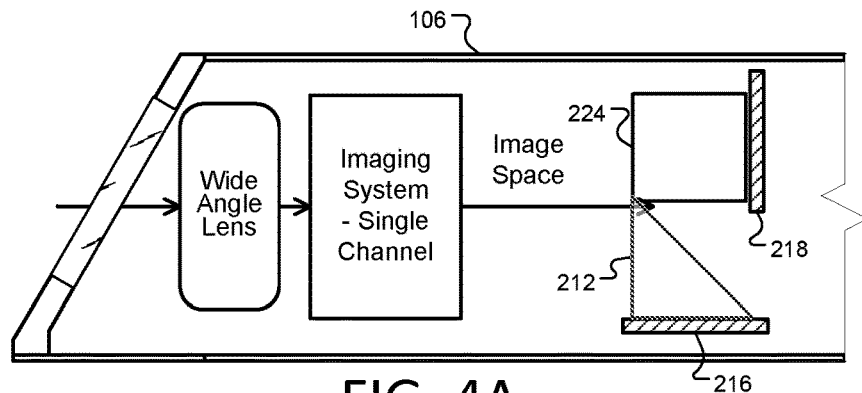
FIGS. 4A-D are cross section diagrams of several example variations of sensor and light directing element placements in the scope distal end portion.

As can be understood, the different portions of light make up different areas from the common image light fed to image space 211, and provide different areas of the image viewable through the scope. The image light may be maintained in the same focal conditions through both prisms 213 so that the two partial images can be easily reconstructed by having identical resolutions. It is not necessary in all embodiments that the two prisms 213 or light directing elements 12 or the imaging sensors be identical or symmetrical. For example, a non-symmetrical embodiment is shown in FIG. 4A.

Figure 3A:
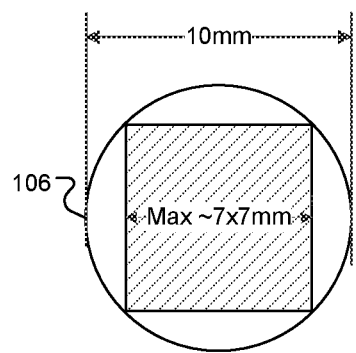
FIGS. 3A-D are cutout diagrams from various perspectives showing example sensor placements.

Referring to FIGS. 3A-3D, several different sensor arrangements are depicted. In FIG. 3A, a theoretical maximum area square sensor is shown in the conventional configuration with the sensor array oriented perpendicular to the longitudinal axis of the endoscope. The sensor area is approximately 7×7 mm, and is the largest that will fit into a 10 mm cylindrical scope tip 106. Of course, in practice sensors include packaging and the associated electronics usually included on a circuit board to which the sensor array is mounted, and so the depicted theoretical maximum area is not reached in practice.

Figure 3B:
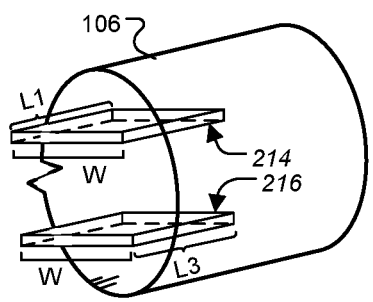

In reality, 7×7 mm a sensor module will provide an array with a certain percentage smaller sensor. However, two such sensors can greatly increase the image resolution available if they are employed together in alternative positions inside the scope distal end 106, as depicted in the example diagrams of various embodiments of the in invention in FIGS. 3B, 3C, and 3D. FIG. 3B shows a perspective cutaway diagram from beside and forward of a scope distal end 106, with the cover glass and optics cutaway. As can be seen, sensors 214 and 216 are fit into the cylindrical scope tip, and while this does not allow an increased width, it does allow an increased length or height of the total area sensed, which can be as high as the sum of both lengths, L1+L3 as shown.

It is noted that preferably a square sensor is not used, but a commercially available rectangular sensor with an aspect ratio according to one of the several HD aspect ratios (such as, for example, the 16:9 aspect ratio used for 1920×1080 HD, or the 4:3 aspect ratio used for 1440×1080). In such a case, a higher resolution can be achieved by orienting such HD sensors horizontally with respect to the diagrams shown, where for example in FIG. 3B, L1 and L3 is the physical length of the 1080 dimension of the sensor array, while the width W is the physical width of the 1920 dimension of the sensor array. A sensor may also be fit favorably in the cylindrical scope distal tip 106 with the shorter dimension of the sensor along the W side, and the longer as the L1 or L3 side.

The prior arrangement may be preferred to provide a sensor field better matched to a circular field of view of wide-angle (e.g., fisheye) implementations of the lens 204. Further, while currently the best available sensors sizes for the desired scope diameters (10 mm being most common but other diameters are also used such as 4 mm or 5 mm) are HD resolution sensors, future generations such as 4K or UHD sized sensors may also be placed in the depicted arrangements to increase the image resolution still further. Further, custom sensors that are square or have other shapes, including curved sensors (e.g., curved sensors that reduce or eliminate Petzval field curvature), may be employed having other desired sizes as long as they are able to fit inside whatever scope diameter is used.

Figure 3C:
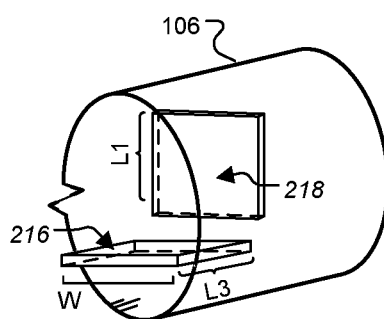

FIG. 3C shows a similar perspective cutaway diagram for the arrangement of FIG. 4A. Sensor 216 has a length L3 and width W, and sensor 218 has length L1 and width W. Similar to sensor 214, sensor 218 may be square or have a rectangular aspect ratio such as HD, UHD, 4K, etc., with the preferred orientation of the shorter sensor array dimension being L1 and the longer being W, but switching these edges may also be done.

Figure 3D:
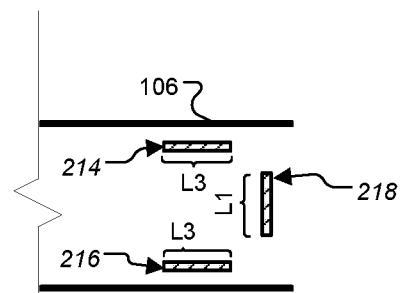

FIG. 3D is a cutaway cross section diagram of another arrangement in which three sensors are employed, which may be used to provide an even taller sensed image allowing electronic panning along the vertical dimension of the field of view or allowing display of an even taller total sensed field of view than the improved version of FIGS. 3B and 3C. Of course, in all the embodiments herein, the relative position may be rotated around the scope axis with the horizontal resolution increased rather than the vertical. As depicted, a sensor 214 has length L3, sensor 218 has length L1, and sensor 216 has length L3. Identical sensors may be used making L1 and L3 identical. The vertical resolution obtainable with this arrangement is a maximum of the combined vertical resolutions of all of these sensors, L3+L1+L3, while the horizontal resolution remains as the original horizontal resolution along the W dimension. The arrangement of FIG. 3D may be oriented with the shorter sensor array side as L1 or L3, and the longer sensor array dimension as W (the dimension into the drawing).

FIG. 4A is a cross sectional diagram of a scope distal end portion 106 mostly similar to that in FIG. 2A, except that a different construction of light directing elements is employed, which direct light to sensors 216 and 218 in a different, non-symmetrical arrangement. The cover glass, lens, and single channel imaging system similar to those of FIG. 2A. In this version, a different arrangement of two image sensors, 216 and 218, is shown with the sensors positioned as described with regard to FIG. 3C. In this version a right angle or triangular prism 212 is positioned in image space 211 of the optical channel assembly to receive the first portion of the image light from the wide angle lens 104 and direct it toward the image sensor 216, and sensor 218 is positioned to receive a second portion of the image light corresponding to second, different area of the image. A cube prism or rectangular prism 224 is arranged in front of sensor 218 to help maintain similar focus conditions and path length to the light passing through prism 212.

In some versions, a combined prism similar to prisms 212 and 224 may be used in which a portion of the prism acts as a beamsplitter to allow some light to pass through straight to sensor 218, while other light is reflected to sensor 216. Such a structure can allow a few rows of pixels toward the front edge of sensor 216 and the lower edge of sensor 218 to view the same area, allowing a digital image processor to align the images to combine them more accurately in case of alignment variations in the prisms or sensors.

Figure 4B:
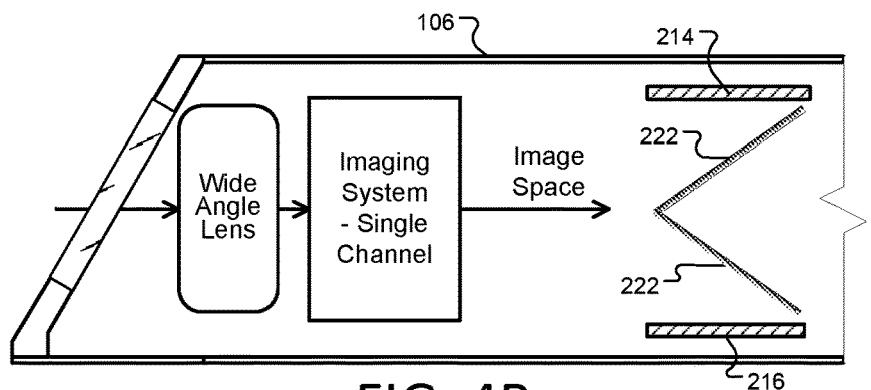

FIG. 4B is a cross sectional diagram of another scope distal end portion 106, mostly similar to that in FIG. 2A, but with a different type of light directing element. In this embodiment, a pair of mirrors 222 is used to reflect light from the image space 211 onto sensors 214 and 216. The mirrors may be mounted at a 135 degree angle relative to the longitudinal axis of the endoscope to reflect light from the image space to the sensors with the sensor arrays oriented parallel to the scope axis.

Figure 4C:
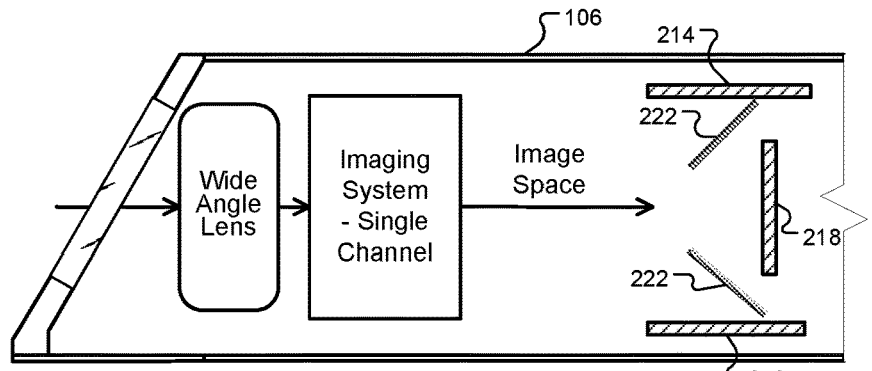

FIG. 4C is a cross section diagram of another example scope distal end portion, this embodiment using mirrors as light directing elements. 222 to reflect a first portion of the image light upward to sensor 214, reflect a second portion of the image light downward to sensor 216, and allow the middle portion of the sensor light to pass to sensor 218.

Figure 4D:
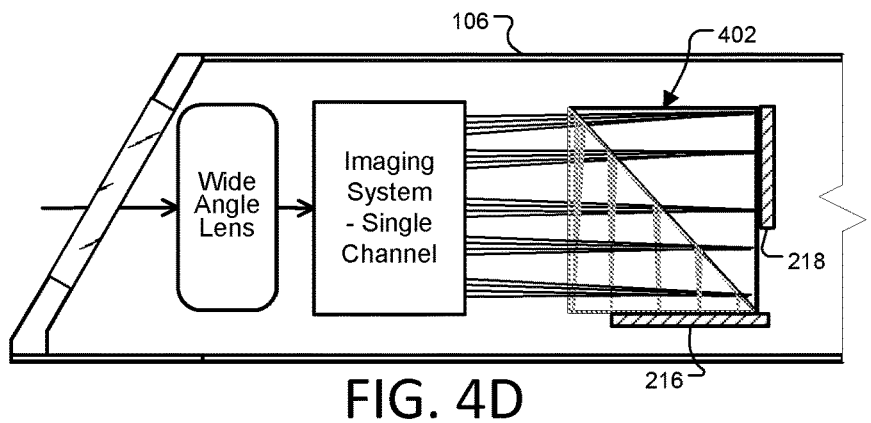

FIG. 4D is a cross section diagram of yet another example, in which a beam splitting prism is used as a light directing element. In this embodiment, a beam splitter prism cube 402 is mounted in the distal end 106 to receive the image light from the single channel imaging system. The prism cube 402 may be constructed with suitable prisms to split the incoming light to the two sensors 216 and 218, each positioned to receive a portion of the image light corresponding to a different portion of the optical channel assembly field of view.

For example, the prism 402 may be constructed with two right angle prism joined together, with a dielectric, achromatic beamsplitter coating along the interface between the prisms. As can be seen in the light ray diagram, the light is split with 50% of the light reflected downward while the other 50% is passed straight through the prism 402. Alternatively, the reflectivity of the beamsplitter may vary spatially so that the portions of light reflected to the two sensors may differ from one field position to another. Sensor 218 is positioned to receive light covering at least the upper half of the optical channel assembly field of view, while sensor 216 is positioned to receive redirected light covering at least the lower half of the optical channel assembly field of view. As shown, each sensor receives light from more than half of the field of view, allowing the images received to overlap so that an image based on the entire field of view may be constructed because the lower-depicted edge of sensor 218 and the left depicted edge of sensor 216 receive split versions of the same light rays.

Figure 5:
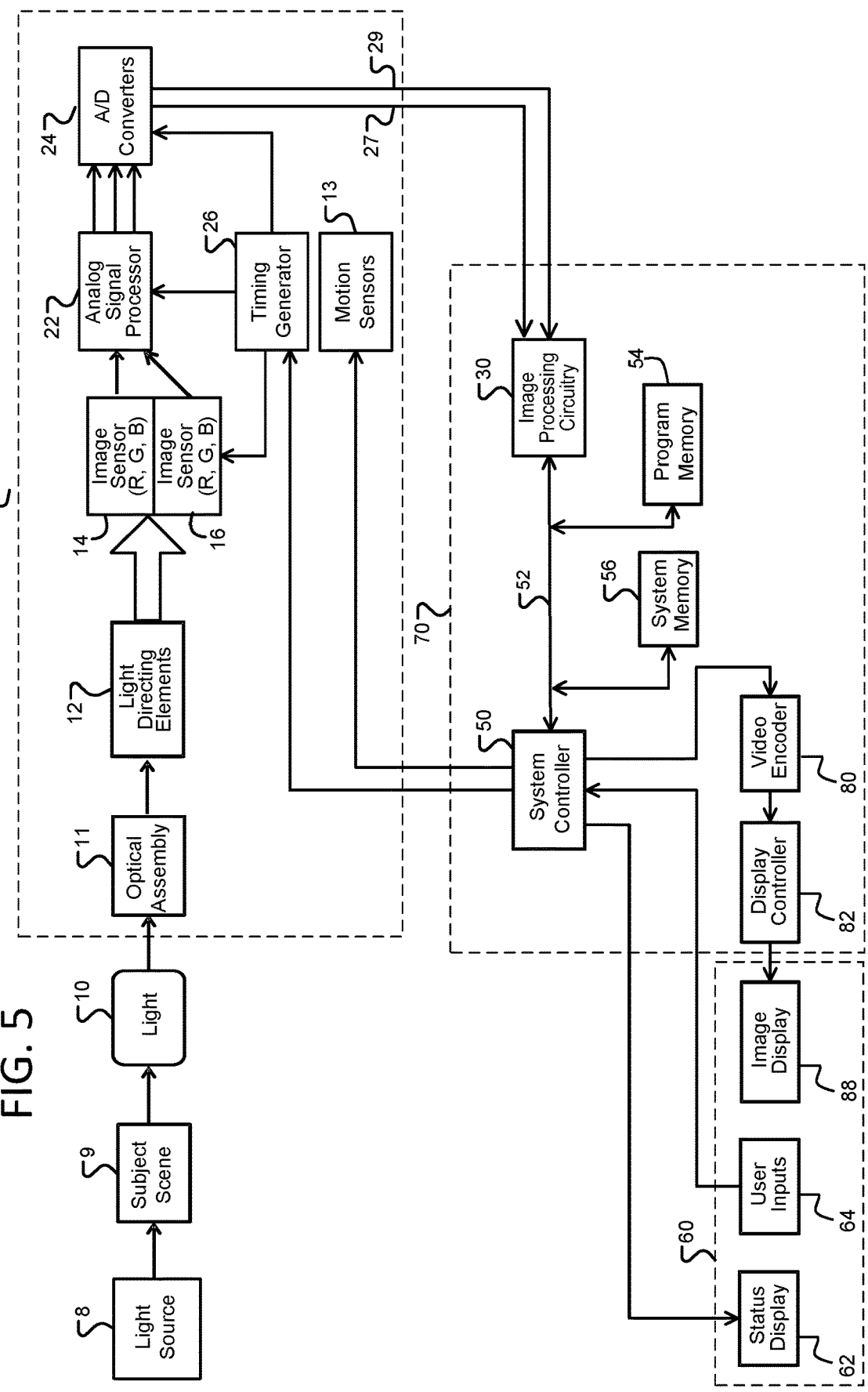
FIG. 5 is a block diagram of an optical instrument system according to an example embodiment of the present invention.

FIG. 5 is a block diagram of an optical instrument system according to an example embodiment of the present invention. While this example circuit is shown for an endoscope, the present invention is applicable to more than one type of medical scope instrument, but typically is applicable for scope applications that employ image capture at the instrument distal tip, such as endoscopes, borescopes, or exoscopes, for example.

A light source 8 illuminates subject scene 9 and light 10 reflected from (or, alternatively, as in the case of certain fluorescent or digital microscope arrangements, transmitted or emitted by) the subject scene forms an optical image via an optical channel assembly 11, where the light is focused, typically aligned with the scope axis or a desired optical axis, and passed to a distal side of optical channel assembly 11 where light directing elements 12 direct different portions of the light to form different portions of the image on two solid-state image sensors 14 and 16.

In the present invention, optical channel assembly 11 includes a single-channel imaging system and may be constructed according to a large variety of known methods suitable for placement in a scope distal tip, including the preferred optical channel assembly of FIG. 2B. Image sensors 14 and 16 convert the incident light to an electrical signal by, for example, integrating charge for each picture element (pixel). The image sensors 14 and 16 may be active-pixel type complementary metal oxide semiconductor sensors (CMOS APS) or a charge-coupled devices (CCD), to give just two possible examples. The output analog signal from the image sensors is processed by analog signal processor 22 and applied to analog-to-digital (A/D) converter 24 for digitizing the analog sensor signals. In some versions (typically CMOS designs), the analog signal processing and A/D converters may be integrated into individual sensor models attached to each sensor 14 and 16.

The system's camera 28 generally includes timing generator 26, which produces various clocking signals to select rows and pixels and synchronizes the operation of image sensors 14 and 16, analog signal processor 22, and A/D converter 24. One or more motion sensors 13 such as, for example, an accelerometer, gyro, or magnetometer, may be mounted in the endoscope shaft, tip, or handle to aid in detecting rotation of the endoscope. A scope distal tip electronic assembly typically houses image sensors 14 and 16, while the locations of each of analog signal processor 22, the A/D converter 24, and the timing generator 26 may vary, for example in the scope handle 102 or partially integrated into the distal tip electronic assembly. The functional elements of the camera 28 may be fabricated as a single integrated circuit as is commonly done with CMOS image sensors or they may be separately-fabricated integrated circuits.

The system controller 50 controls the overall operation of the image capture device based on a software program stored in program memory 54. This memory can also be used to store user setting selections and other data to be preserved when the camera 28 is turned off. Data connections 27 and 29 carry the digital image data of image sensors 14 and 16, respectively, to image processing circuitry 30, which may be integrated with system controller 50 in some versions, or may be a separate programmable logic device or data processor. A data bus 52 provides a pathway for address, data, and control signals. In some variations, data bus 52 may also carry data connections 27 and 29.

Image processing circuitry 30 performs image processing operations including the operations to combine the partial images from image sensors 14 and 16, and to perform rotation functions as further described below. Processed image data are continuously sent to video encoder 80 to produce a video signal. This signal is processed by display controller 82 and presented on image display 88. This display is typically an HD, UHD, or 4K format liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 may manage the graphical user interface (GUI) presented on one or more of the displays (e.g. on image display 88). The GUI typically includes menus for making various option selections.

Image processing circuitry 30, system controller 50, system and program memories 56 and 54, video encoder 80, and display controller 82 may be housed within camera control unit (CCU) 70. CCU 70 may be responsible for powering and controlling light source 8 and/or camera 28. As used herein "CCU" refers to units or modules that power, receive data from, manipulate data from, transmit data to, and/or forwards data from optical instrument cameras. CCU functionalities may be spread over multiple units known as, for example, a "connect module", "link module", or "head module".

Figure 6:
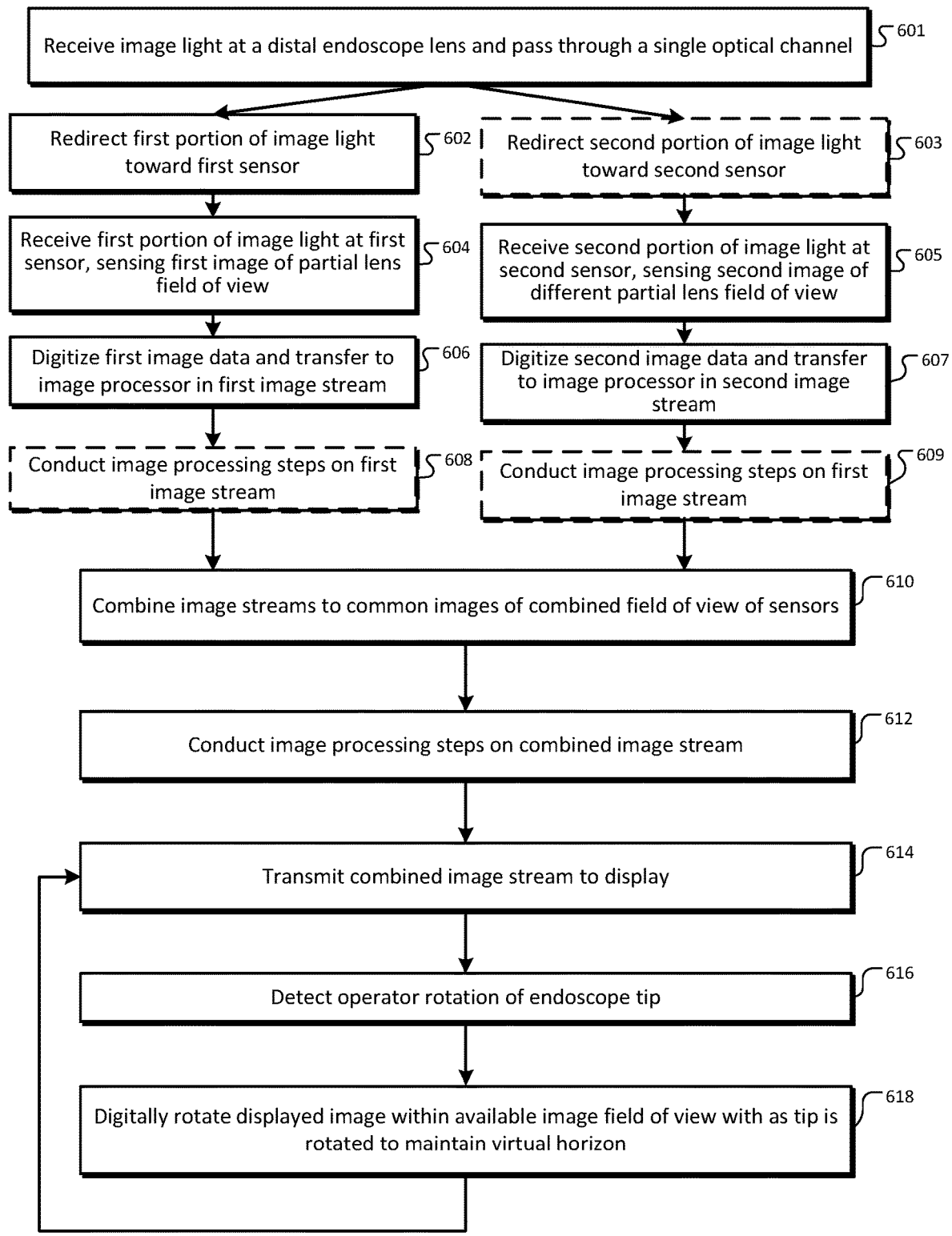
FIG. 6 is a flowchart of an example process for combining and rotating the partial images received from the multiple sensors according to some embodiments.

FIG. 6 is a flowchart of an example process for combining and rotating the partial images received from the multiple sensors according to some embodiments, which may be employed with the example hardware and camera designs herein, or may be employed with other hardware designated with a similar purpose, such as software program code executed by a GPU or other image processor. The depicted process starts at block 601 with receiving image light at a distal lens of an optical assembly and passing the image light through a single optical channel.

Next at blocks 602, the process redirects a first portion of the image light at a non-zero angle to the longitudinal axis of the endoscope toward the first sensor. A second portion of the image light may also be redirected at a non-zero angle to the longitudinal axis of the endoscope at block 603, or it may pass straight to the second sensor in some embodiments, so block 603 is has a dotted border as being optional. As can be understood blocks 602 and 603 may be performed by two different light directing elements or a single light directing element such as a compound prism.

At blocks 604 the process receives the first portion of the image light from the optical channel assembly with the first image sensor, the first portion of the image light forming a first image of a first part of the field of view of the distal lens. Simultaneously at block 605 the process receives the second portion of the image light from the optical assembly with the second image sensor, the second portion of the image light forming a second image of a second part of the field of view of the distal lens, the second part of the field of view substantially different from the first part of the field of view. The first and second images may have a partially overlapping field of view or not.

The depicted process blocks that are in parallel are typically performed with parallel processing, as are many of the other processing functions in preferred designs. At blocks 608 and 609, the process may perform one or more image processing steps, with these shown in dotted lines to indicate it is optional in some embodiments. Next, at block 610, the process includes combining the first and second images to produce an image of the combined field of view of the sensors. The combined image typically has a higher resolution than would otherwise be possible with a single sensor. This block may include steps to adjust for relative misalignment of the sensors, such as applying a rotation to image data from one or both sensors (preferably provided in calibration of the instrument), and may include recognizing edges at the edges of the first and second images so that those edges can by aligned in the combined image.

If overlapping pixels are available as described above, the process may include cross-correlating these overlapping pixels to find the highest point of alignment, or applying a shift to one or both of the images to account for an offset detected in calibration. Such edge detection and correlation are known in the art and will not be further described. The combined image is then subjected (at block 612) to image processing such as dynamic range adjustment, filtering, color range adjustment, feature recognition, and any other suitable image processing techniques for endoscopic imaging.

The combined image or a selected sub-image from the total combined image are transmitted to an electronic display for display to the operator at block 614, and may also be recorded and saved with any suitable video or image recording format. The entire image is then available for viewing, image processing, and manipulation according to any suitable medical imagery techniques. In some scenarios, the entire combined image may be displayed, while in others an HD aspect ratio image smaller than the total image may be selected out of the entire combined image for display, allowing panning or rotation of the image. A diagram of such an image may be seen in FIG. 7, in which the combined field of view of a first sensor 214 and a second sensor 216 are shown each with a different fill pattern. The circle 130 represents the area of the image light coming from the round lens, and it can be seen in the arrangement of FIG. 5 that in this version the entire view 130 of the lens is captured by the combination of the two sensors 214 and 216 (or three or more sensors as according to various embodiments discussed above).

Referring again to FIG. 6, while displaying the combined image stream, at block 616 the process detects the physical rotation of the scope distal end, which may be through sensors such as motion sensors 13 and recognized by the system controller 50. In some embodiments, detecting rotation may also be done by detecting such rotation in the received stream of images through image processing. An operator may set the current orientation as the desired viewing orientation through the user interface 64 or through a button on the scope handle, for example, after which the process will digitally rotate the display to make counter-rotations to the displayed images in the opposite direction of the scope physical location to maintain 'virtual horizon' constant viewing orientation as shown at block 618.

Figure 8:
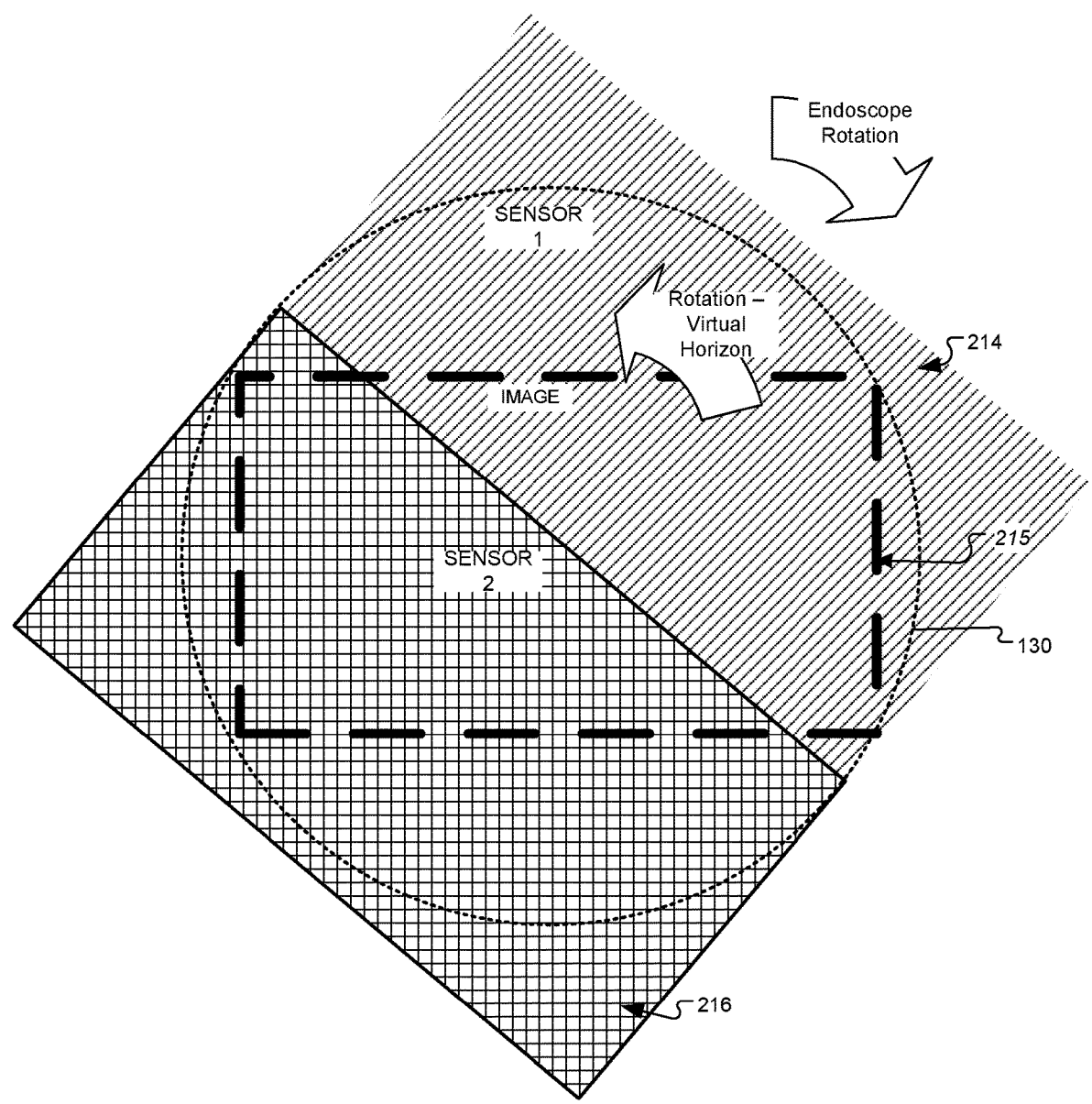
FIG. 8 is a diagram showing digital rotation of a displayed area within the combined image sensor field of view to provide a virtual horizon.

In rotating the display, as shown in the diagram of FIG. 8, the process rotates the displayed view over different portions of the partial images received from the image sensors, in which the combined field of view of a first sensor 214 and a second sensor 216 are shown each with a different fill pattern. As depicted in this example diagram, an operator rotating the endoscope in the clock-wise direction causes the process to counter-rotate the image in the counter-clockwise direction within the available field of view, maintaining the view orientation to avoid the common problem of operator visual disorientation during examination procedures. The opposite physical rotation of course causes an opposite digital rotation. While this version provides a displayed image area that is able to maintain the depicted aspect ratio (16:9) while displaying a full image 215 using data from both sensors, other operating modes may be provided to display a larger portion of the total imaged area, or all of the image area.

Figure 7:
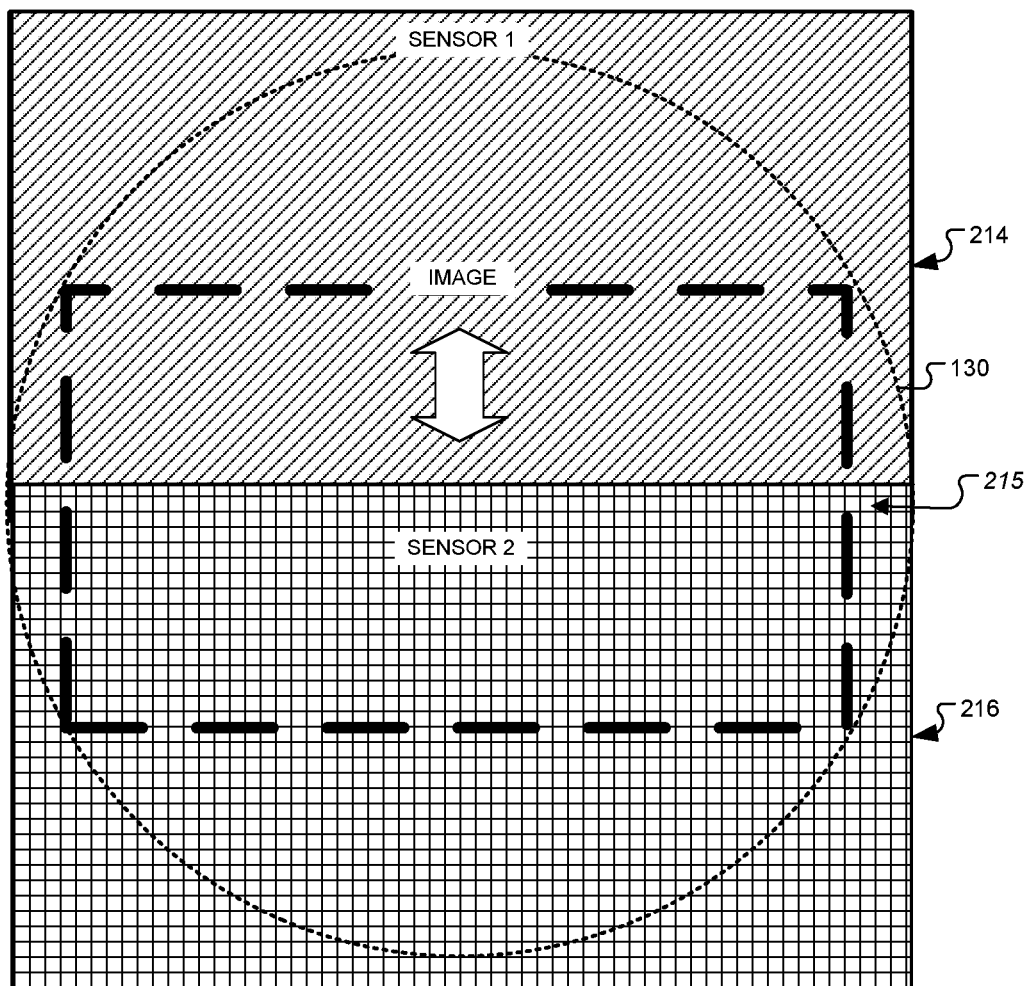
FIG. 7 is a diagram showing a displayed area selected from within the combined image sensor field of view according to an example embodiment.
Figure 9:
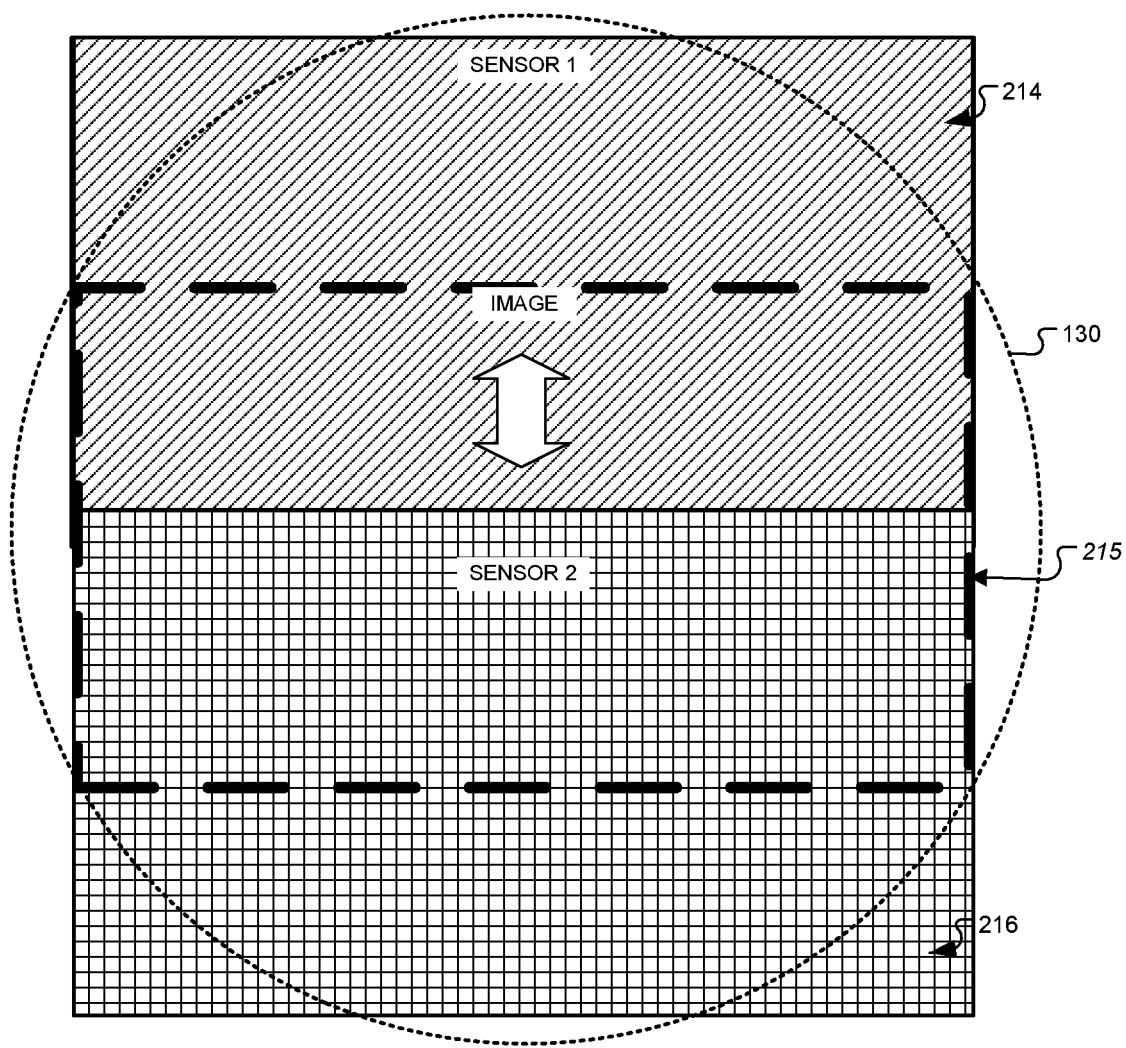
FIG. 9 is an example diagram of another display area scheme showing a larger portion of the available combined image area.

FIG. 9 shows an example diagram of another display area 215 showing a larger portion of the available combined image area. As can be seen from the overlay of the lens field of view 130 on the diagram, this version does not make full use of the lens field of view, but uses more of the sensor data. Digital panning along the combined image may also be provided in any of the embodiments, in which the up/down arrow shown in FIGS. 7 and 9 shows how a display area may be panned along the available combined image data. The vertical direction of the diagram represents the vertical direction of the wide angle lens field of view in the diagram of FIG. 2A. In some versions or modes, rotation of the view may cause "vignetting" or rounded off dark corners or edges where the desired display area exceeds the available image data from the combined image from the sensors. In some implementations a processing unit may correct or modify the distortion characteristics of the image.

Because digital cameras employing endoscopic instruments and related circuitry for signal capture, processing, and correction and for exposure control are well-known, the above description is directed in particular to elements forming part of, or cooperating more directly with, a method and apparatus in accordance with the present invention. Elements not specifically shown or described herein are selected from those known in the art. Certain aspects of the embodiments may be provided in software. Given the system as shown and described according to the invention in the following materials, software not specifically shown, described or suggested herein that is useful for implementation of the invention is conventional and within the ordinary skill in such arts.

The invention being thus described, it will be obvious that the same may be varied in many ways. Such variations are not to be regarded as a departure from the scope of the invention, and all such modifications as would be obvious to one skilled in the art are intended to be included within the scope of the following claims. For example, reference to an endoscope is intended merely as a representative example application and is not intended to be limiting. Implementations include optical scopes such as exoscopes and borescopes. Further, although sensors 214, 216, and 218 are shown as discreet entities, two or more of the sensors may share, for example, a mounting substrate or housing accommodating the two or more sensors.

Further still, although this distribution of imaging device functional control among multiple programmable logic devices, programmable logic devices, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

What is claimed is:

1. An end oscopic instrument comprising:
   (a) a shaft having a distal end portion and a longitudinal axis spanning distal and proximal sides of the distal end portion;
   (b) a single optical channel assembly comprising an objective lens with negative optical power positioned in the distal end portion to collect image light from a single perspective of an object space; generate, in an image space, a single optical image of the single perspective of the object scene; and pass the image light toward the proximal side;
   (c) a first light directing element comprising a beam splitter positioned within the optical channel at a sufficient distance from the objective lens such that the first light directing element is positioned in the image space of the optical channel assembly, the first light directing element positioned to receive a first portion, but not all, of the image light and direct the first portion of the image light, corresponding to a first area of the a collected image, along an optical axis that is non-parallel to the longitudinal axis;
   (d) a first image sensor positioned in the shaft distal end portion to receive the first portion of the image light, wherein the first image sensor is a two-dimensional image sensing array; and
   (e) a second image sensor positioned to receive a second portion of the image light corresponding to a second area of the collected image that is at least substantially different from the first area of the collected image, wherein the second image sensor is a two-dimensional image sensing array.

2. The end oscopic instrument of claim 1, in which the optical channel assembly further comprises a single channel imaging system including at least one lens optically arranged between the objective lens and the first and second image sensor.

3. The end oscopic instrument of claim 1 further comprising a processing unit operatively coupled to the first and second image sensors to receive first and second image data from the sensors and operable to combine images from the first and second image data into composite image of higher resolution than that possible with the first sensor alone or the second sensor alone.

4. The end oscopic instrument of claim 3 further comprising a motion sensor, wherein the motion sensor operable to detect rotation about the longitudinal axis of the distal end portion.

5. The end oscopic instrument of claim 4 further comprising a display unit, and wherein the processing unit is further operable to process the collected image data enabling the display unit to display an image with a constant horizon.

6. The endoscopic instrument of claim 1, wherein the first portion and second portion of the image light overlap, such that each sensor receives light from more than half of the optical image.

7. A method of providing endoscopic images comprising the steps of
   collecting image light at a single perspective from an illuminated object space with a distal lens, with a negative optical power, of a single optical channel assembly, the distal lens placed in a distal end portion of an endoscopic shaft, the optical assembly having a longitudinal axis spanning a distal and a proximal side of the distal end portion;
   passing the collected image light from the distal side of the distal end portion to the proximal side of the distal end portion;
   directing the collected image light into an image space along an optical path of the optical assembly;
   splitting the image light within the image space with a beam splitter positioned within the optical channel at a sufficient distance from the distal lens such that the beam splitter is positioned in the image space of the optical channel assembly;
   directing, with the beam splitter, a first portion, but not all, of the split image light within the image space along an optical path that is not parallel to that of the optical assembly;
   capturing the first portion of the image light with a first two-dimensional image sensor positioned in the shaft distal end portion;
   capturing a second portion of the image light, at least substantially different from the first portion of the image light, with a second two-dimensional image sensor positioned in the shaft distal end portion; and
   combining, with an image processor, the first and second images to produce an image of higher resolution than would be possible with a single sensor.

8. The method of claim 7 wherein the first and second portions of image light partially overlap.

9. The method of claim 7, further comprising, in response to a user rotation of the end oscopic instrument around its shaft, processing collected image data to create an image with a constant horizon and of higher resolution than would otherwise be possible with a single sensor.

10. An endoscopic instrument comprising:
 (a) a shaft having a distal end portion with an inner diameter and a longitudinal axis spanning distal and proximal sides of the distal end portion;
 (b) a single optical channel assembly comprising an objective lens with negative optical power positioned in the distal end portion to collect image light from a single perspective of an object space; generate, in an image space, a single optical image of the single perspective of the object scene; and pass the image light toward the proximal side;
 (c) a first image sensor comprising an image sensing active area mounted on a circuit board, the circuit board having a diagonal length longer than the inner diameter of the of the distal end portion and an area greater than the image sensing active area;
 (c) a first light directing element positioned within the optical channel at a sufficient distance from the objective lens such that the first light directing element is positioned in the image space of the optical channel assembly, the first light directing element positioned to receive a first portion, but not all, of the image light and direct the first portion of the image light, corresponding to a first area of the a collected image, along an optical axis that is non-parallel to the longitudinal axis; and
 (e) a second image sensor, comprising an image sensing active area mounted on a circuit board having an area greater than the image sensing active area, the second image sensor positioned to receive a second portion of the image light corresponding to a second area of the collected image that is at least substantially different from the first area of the collected image; wherein the first image sensor is not coplanar with the second image sensor and is positioned in the shaft distal end portion to receive the first portion of the image light.

11. The endoscopic instrument of claim 10 wherein
 (a) the first image sensor is rectangular with a height L1 and a width W1, and with an image sensing active area with a height l1 and a width w1;
 (b) the second image sensor is rectangular with a height L2 and a width W2 and with an image sensing active area with a height l2 and a width w2;
wherein the values of W1 and W2 are both individually smaller than the inner diameter of the distal end portion, and wherein L1+L2 is greater than the inner diameter of the distal end portion.

12. The end oscopic instrument of claim 10 further comprising an image processing circuitry operable to combine image data received from the sensors into a single image representing an image of the captured single perspective of the object space.

13. The end oscopic instrument of claim 11 wherein the single optical image in image space is circular with a diameter, D, and wherein D is greater than the values of l1 and l2; D is less than or equal the value of w1 and w2; and D is less than or equal to l1+l2.

* * * * *